United States Patent [19]
Kawasaki et al.

[11] Patent Number: 6,040,156
[45] Date of Patent: Mar. 21, 2000

[54] DNA ENCODING GLUCURONYLTRANSFERASE

[75] Inventors: Toshisuke Kawasaki, Hirakata; Shogo Oka, Uji, both of Japan

[73] Assignee: Seikagaku Corporation, Tokyo, Japan

[21] Appl. No.: 09/059,369

[22] Filed: Apr. 14, 1998

[30] Foreign Application Priority Data

May 16, 1997 [JP] Japan ..................................... 9-127065

[51] Int. Cl.$^7$ ............................... C12P 2/06; C12N 9/10; C07H 17/00
[52] U.S. Cl. ..................... 435/69.1; 435/193; 435/320.1; 435/325; 435/252.3; 536/23.2
[58] Field of Search ................................ 435/193, 320.1, 435/325, 252.3, 69.1; 536/23.2

[56] References Cited

PUBLICATIONS

Adams, M.D. et al. "3,400 new expressed sequence tags identify diversity of transcipts in human brain." Nature Genetics (Jul. 1993), vol. 4, pp. 256–267, Jul. 1993.

*Primary Examiner*—Karen Cochrane Carlson
*Attorney, Agent, or Firm*—Oblon, Spivak, McClelland, Maier & Neustadt, P.C.

[57] ABSTRACT

A DNA having a base sequence encoding a polypeptide of a glucuronyltransferase characterized in that:

A) action:
said glucuronyltransferase transfers glucuronic acid from a glucuronic acid donor to a glucuronic acid acceptor;

B) substrate specificity:
said glucuronyltransferase selectively transfers glucuronic acid to N-acetyllactosamine residue of asialoorosomucoid and neural cell adhesion molecule;

C) optimum reaction pH:
said glucuronyltransferase has an optimum pH of about 6.0 to 6.5 (in 100 mM, MES buffer at 37° C.);

D) inhibition and activation:
said glucuronyltransferase is activated by $Mn^{2+}$ and the activity is maintained in the presence of 5 mM of neolactotetraose-phenyl-$C_{14}H_{29}$; and E) molecular weight:
said glucuronyltransferase has a molecular weight of about 45,000 dalton measured by reductive SDS-polyacrylamide gel electrophoresis and a molecular weight of about 90,000 dalton measured by gel filtration.

15 Claims, 3 Drawing Sheets

FIG. 1

```
Peptide 1        Val  Pro  Asn  Leu  His  Trp                    3'
pr. 1-s    5'    GTI  CCT  AAT  TTT  CAT  TGG
                      C    C    C    C
                      A         A
                      G         G Peptide 2        Tyr  Phe  Ala  Asp  Asp  Asp  Asn  Thr  Tyr     5'
pr. 1-ao   3'                   CTA  CTA  CTA  TTA  TGT  AT
                                G    G    G    G    C
                                                    A
                                                    G pr. 1-ai   3'    ATA  AAA  CGT  CTA  CTA  CT                     5'
                 G    G    C    G    G
                           A
                           G pr. 2-so   5'    TAT  TTT  GCT  GAT  GAT  GA                     3'
                      C    C    C    C    C
                                A
                                G pr. 2-si   5'         TTT  GCT  GAT  GAT  GAT  AA                3'
                           C    C    C    C
                                A
                                G Peptide 3        Met  Ala  Gly  Phe  Ala  Val                    5'
pr. 2-a    3'    TAC  CGT  CCT  AAA  CGT  CA
                      C    C    G    C
                      A    A         A
                      G    G         G
```

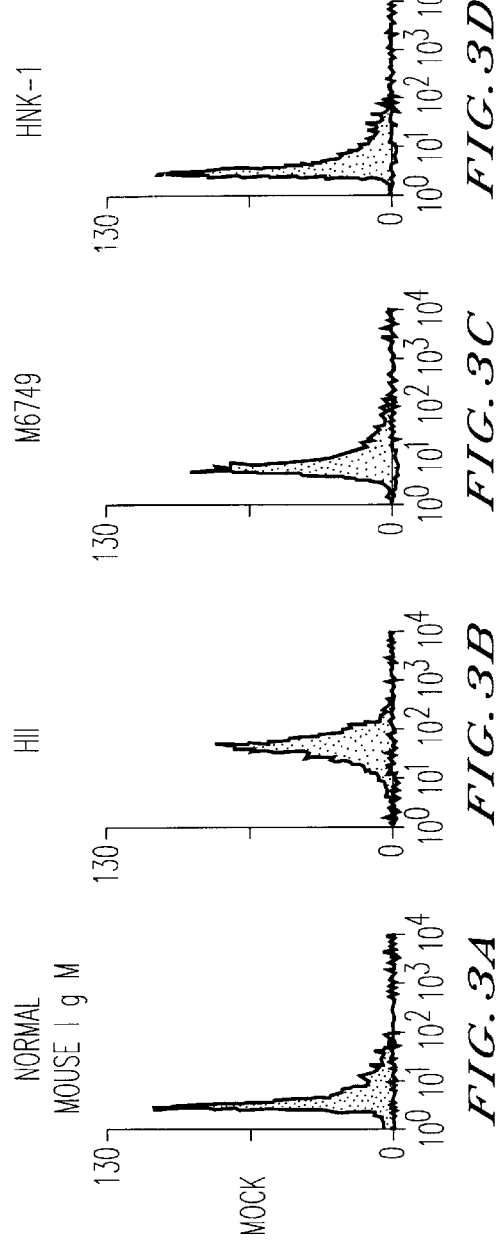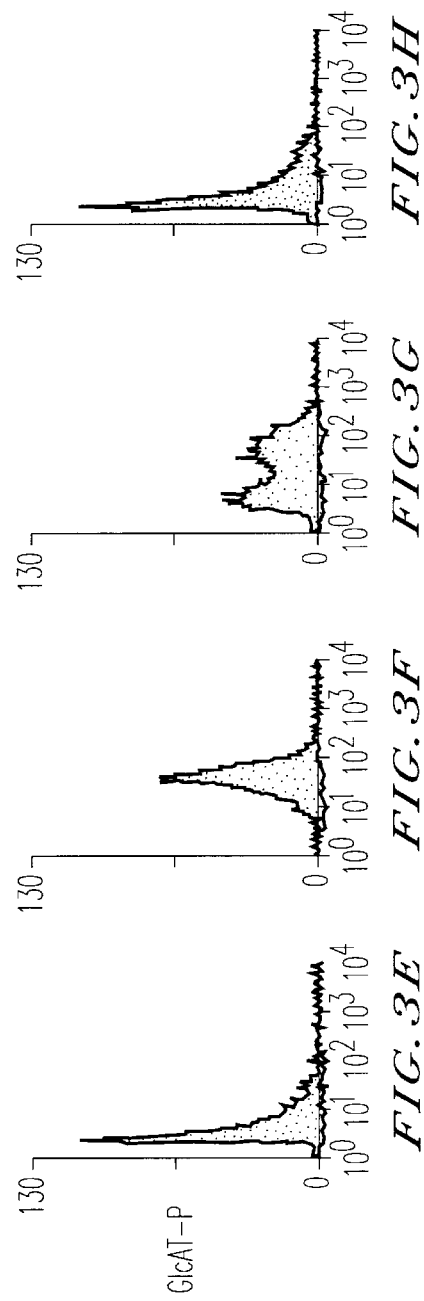

DNA ENCODING GLUCURONYLTRANSFERASE

BACKGROUND OF THE INVENTION

1. Field of the Invention

The present invention relates to a novel DNA having a base sequence encoding a glucuronyltransferase. In particular, the present invention relates to a DNA encoding the glucuronyltransferase involved in synthesis of the HNK-1 epitope, which is characteristically expressed on neuronal cells or immune cells.

2. Discussion of Background

Regarding the HNK-1 antigen, which exclusively exists in the nervous system and on immunocytes, it is known that the antigen plays important roles in development of the nervous system and cell adhesion and that peripheral neuropathy attributable to autoimmune disease induces an increase of antibodies against the antigen (Pharmacia, 32, 11, 1361–1369 (1996)). The expression of the antigen by natural killer T cells (NK cells) and the selective attraction by tumor cells of T cells expressing the antigen (Clin. Exp. Immunol., 102, 159–166 (1995)) indicate that the antigen is involved in recognition and elimination of foreign matters by NK cells. However, the HNK-1 antigen expressed on NK cells has been used only as a marker of the NK cells, and its functions are quite unknown. The HNK-1 antigen has 3-sulfated glucuronic acid unlike most glycoproteins and glycolipids, and this structural feature indicates that biosynthesis of the antigen involves a glucuronyltransferase. Glucuronyltransferases are roughly classified into two: glucuronyltransferase-L and glucuronyltransferase-P (J. Biol. Chem., 267, 32, 22711–22714 (1992)), but little is known about these enzymes so far.

As discussed above, the HNK-1 antigen is clearly involved in development and disorder of the nervous system, but their mechanisms have not been elucidated yet. Especially, peripheral neuropathy attributable to autoimmune disease is a serious problem, but development of its curative treatment is retarded. In this respect, clarification of these mechanisms is desired, too. The mechanisms of the recognition and elimination of foreign matters by immunocytes are still unclear, and elucidation of the functions of the HNK-1 antigen is necessary to understand the mechanisms.

For the purpose of elucidating the functions of the HNK-1 antigen, the present inventors successfully extracted and isolated glucuronyltransferase-P (hereinafter referred also to "GlcAT-P") which controls the rate-determining reaction in biosynthesis of the HNK-1 antigen from living tissues, but through complicated procedures and only in small amounts. Further, since cloning of a cDNA of the enzyme had not succeeded, it was impossible to elucidate the functions of the HNK-1 antigen, especially, in living cells.

In view of these problems, for the purpose of earlier elucidation of the functions of the HNK-1 antigen, the present inventors conducted extensive research to obtain the gene of glucuronyltransferase-P which enables mass production of glucuronyltransferase-P which is the enzyme controlling transfer of glucuronic acid, which determines the rate of the synthesis of the HNK-1 antigen in vivo and in vitro and elucidation of the functions of the enzyme. Consequently, they succeeded in cloning of a cDNA of the enzyme and expression of the cDNA as GlcAT-P, and have accomplished the present invention.

SUMMARY OF THE INVENTION

Namely, the present invention provides a DNA having a base sequence encoding a polypeptide of a glucuronyltransferase characterized in that:

A) action:
said glucuronyltransferase transfers glucuronic acid from a glucuronic acid donor to a glucuronic acid acceptor;

B) substrate specificity:
said glucuronyltransferase selectively transfers glucuronic acid to N-acetyllactosamine residue of asialoorosomucoid and neural cell adhesion molecule;

C) optimum reaction pH:
said glucuronyltransferase has an optimum pH of about 6.0 to 6.5 (in 100 mM, MES buffer at 37° C.);

D) inhibition and activation:
said glucuronyltransferase is activated by $Mn^{2+}$ and the activity is maintained in the presence of 5 mM of neolactotetraose-phenyl-$C_{14}H_{29}$; and E) molecular weight:
said glucuronyltransferase has a molecular weight of about 45,000 dalton measured by reductive SDS-polyacrylamide gel electrophoresis and a molecular weight of about 90,000 dalton measured by gel filtration.

The present invention also provides a DNA having a base sequence encoding at least part of the polypeptide of a glucuronyltransferase having an amino acid sequence of SEQ ID NO:2 in which substitution, deletion, addition or transposition of at least one amino acid residues may be made so as not to be virtually harmless to the transfer of glucuronic acid from a glucuronic acid donor to asialoorosomucoid being a glucuronic acid acceptor.

As specific examples of the DNA of the present invention, DNAs having base sequences encoding the amino acid sequences of amino acids 1 to 347 and of amino acids 75 to 347 in SEQ ID NO:2 may be mentioned.

Further, the present invention provides a method of producing a polypeptide, which comprises culturing cells transformed with the DNA according to claim 1 by using an appropriate culture medium, allowing the cells to produce and accumulate the polypeptide of the glucuronyltransferase encoded by the base sequence of the DNA in the cultured material, and isolating the polypeptide from the cultured material.

BRIEF DESCRIPTION OF THE DRAWINGS

FIG. 1 shows a partial amino acid sequence of GlcAT-P and the base sequences of primers for PCR.

FIG. 3 shows the effects of expression of GlcAT-P on the staining profiles of various antibodies.

DETAILED DESCRIPTION OF THE PREFERRED EMBODIMENTS

Figure 2:
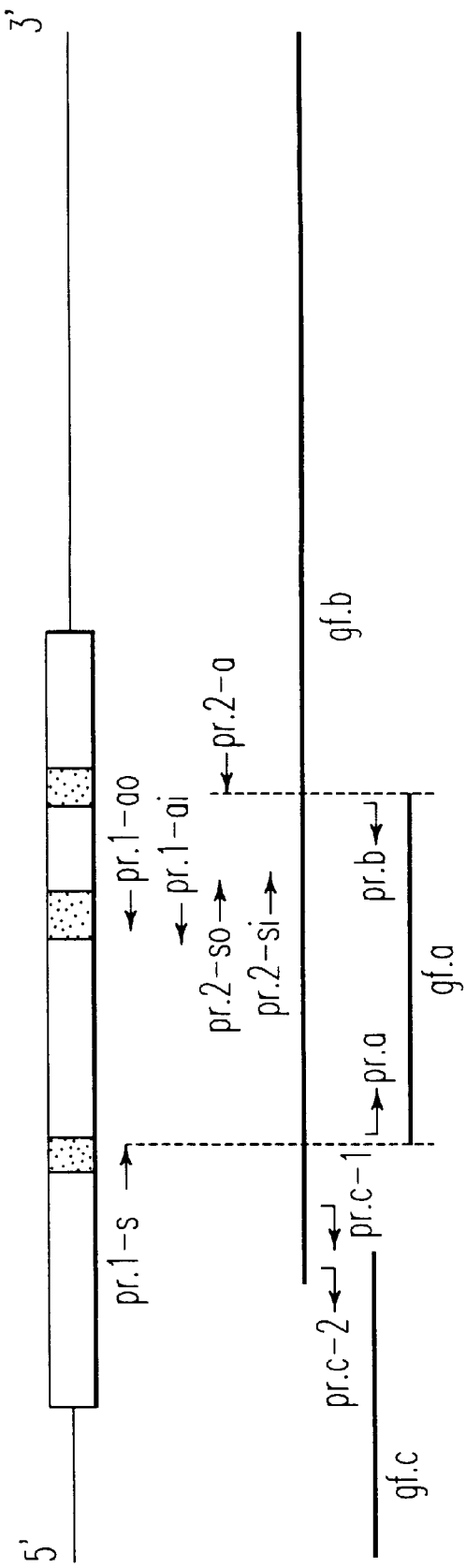
FIG. 2 indicates the locations of DNA fragments and primer sequences.

Now, the mode of carrying out the present invention will be described.

<1> The DNA of the present invention having a base sequence encoding the polypeptide chain of a glucuronyltransferase (the DNA of the present invention) The glucuronyltransferase having the polypeptide chain encoded by the base sequence of the DNA of the present invention is the glucuronyltransferase-P which the present inventors isolated from the rat brain (Oka, S., Terayama, K., Kawashima, C., and Kawasaki, T. (1992) J. Biol. Chem. 267, 22711–22714) and has the following physical and chemical properties:

A) action:
said glucuronyltransferase transfers glucuronic acid from a glucuronic acid donor to a glucuronic acid acceptor;

B) substrate specificity:
  said glucuronyltransferase selectively transfers glucuronic acid to N-acetyllactosamine residue of asialoorosomucoid and neural cell adhesion molecule;
C) optimum reaction pH:
  said glucuronyltransferase has an optimum pH of about 6.0 to 6.5 (in 100 mM, MES buffer at 37° C.);
D) inhibition and activation:
  said glucuronyltransferase is activated by $Mn^{2+}$ and the activity is maintained in the presence of 5 mM of neolactotetraose-phenyl-$C_{14}H_{29}$; and
E) molecular weight:
  said glucuronyltransferase has a molecular weight of about 45,000 dalton measured by reductive SDS-polyacrylamide gel electrophoresis and a molecular weight of about 90,000 dalton measured by gel filtration.

The activity of the glucuronyltransferase-P can be measured by the method disclosed in the above-mentioned paper. The glucuronic acid acceptor specificity for the N-acetyllactosamine residue of asialoorosomucoid and neural cell adhesion molecule generally means that the enzyme transfers glucuronic acid to N-acetyllactosamine residues of the above-mentioned glucuronic acceptors used as an acceptor with a at least five-fold higher activity than to N-acetyllactosamine residues of glycolipid acceptors. The optimum pH is measured in 100 mM of MES buffer instead of 100 mM HEPES buffer, which was used as the reaction solution in the paper. Inhibition or activation is recognized from the activity measured with various test substances added to the reaction solution. The enzyme is activated appreciably by at least 20 mM of $Mn^{2+}$. The enzyme maintains at least 70% of the activity in the presence of a glycolipid inhibitor such as neolactotetraose-phenyl-$C_{14}H_{29}$ as compared with the activity in the absence of the inhibitor.

In general, the glucuronyltransferase-P is also characterized in that its activity is considerably low in the absence of bivalent cations, that it is inhibited by N-ethylmaleimide, and that these activated by sphingomyelin.

The molecular weight is measured under conditions generally employed for enzyme proteins.

The DNA of the present invention was isolated for the first time on the basis of the present invention, and its base sequence is not particularly limited as long as it encodes at least part of the polypeptide of GlcAT-P. In the amino acid sequence encoded by the base sequence of the DNA of the present invention, substitution, deletion, addition or transposition of at least one amino acid residues may be made so as not to be virtually harmless to the transfer of glucuronic acid from a glucuronic acid donor to asialoorosomucoid as a glucuronic acid acceptor, and the DNA of the present invention include any of such DNAs. The activity is measured by known methods (J. Biol. Chem., 267, 22711–22714 (1992)), and it is easy for a person skilled in the art to select an amino acid sequence including substitution, deletion, addition or transposition of at least one amino acids which is substantially harmless to the activity of the enzyme, based on the desired enzymatic activity.

As the DNA of the present invention, a DNA having a base sequence encoding the amino acid sequence of amino acids 1 to 347 in SEQ ID NO:2 is specifically mentioned and preferred. As the base sequence of the DNA of the present invention, part or all of the base sequence represented by SEQ ID NO:1 is specifically mentioned and preferred. As such a DNA, a DNA having a base sequence of nucleotides 195 to 1235 in the sequence list is specifically mentioned.

According to the base sequence of SEQ ID NO:1, the open reading frame of the GlcAT-P cDNA contains seven in-frame ATG codons. Around the first ATG codon of the base sequence, there are a purine at the −3 position and G (guanine) at the +4 position like around the common sequence of the translation initiation site for eucaryotic cells. This is consistent with Kozak's rules for efficient translation (Kozak, M. (1986) Cell, 44, 283–292). Because the base sequence has purines three nucleotides upstream from the second and fifth to seventh ATG codons (G, A (adenine), G and G, respectively) and has C (cytosine) instead of purines three nucleotides upstream and G for nucleotides downstream from the fourth ATG codon. That indicates that any ATG codons except for the third one might function as an initiation codon.

On the other hand, the reading frame for β-1,4-galactosyltransferase is known to have two ATG codons (Nakazawa, K. et al. (1988) J. Biochem. 104, 165–168, Shaper, N. et al. (1988) J. Biol. Chem., 263, 10420–10428). Shaper et al. also suggested that translation from the two initiation sites produces long and short forms of β-1,4-galactosyltransferase. Further, Lopez et al. presented evidence which suggests that the long one exists in the plasma membrane preferentially and the short one exists mainly in the Golgi apparatuses (Lopez, L. et al. (1991) J. Biol. Chem., 266, 15984–15991). More than one ATG codons might function as the initiation codon for GlcAT-P, too, but it is not uncertain. Anyway, the present invention covers DNAs starting from the second and fourth to seventh ATG codons because it does not matter which ATG codon functions as the initiation codon as long as the above-mentioned glucuronyltransferase-P is encoded.

The single open reading frame starting from the first ATG codon predicts a protein of 39,706 Da composed of 347 amino acid residues. The hydrapathy analysis of the amino acid sequence detected one noticeable hydrophobic region composed of seventeen amino acid residues 20 to 36 from N-terminus and predicts a type II transmembrane protein having a transmembrane domain. Next to the transmembrane domain, there is a region which contains a relatively large amount of proline. Proline-rich regions like this are found in some other glycosyltransferases and presumably form the neck regions connecting transmembrane domains and catalytic domains. Accordingly, it is thought that it does not matter to the activity if the length between the N-terminus and the region is reduced, and if most of the transmembrane domain is cut off, a soluble form of glucuronyltransferase is produced. The present invention also covers DNAs encoding at least part of the amino acid sequence of such a soluble form of glucuronyltransferase. As such a DNA encoding such an amino acid sequence, a DNA having a base sequence encoding the amino acid sequence of amino acids 75 to 347 in SEQ ID NO:2 may be mentioned.

The DNA of the present invention may contain substitution, deletion, addition or transposition of nucleotides which leads to substitution, deletion, addition or transposition of at least one amino acid residues as long as the activity of the polypeptide, GlcAT-P, encoded by the base sequence of the DNA which transfers glucuronic acid from a glucuronic acid donor to sugar residues of glycoproteins being a glucuronic acid acceptor is not substantially impaired. Substitution, deletion, addition or transposition of nucleotides can be made by replacing part of an intact DNA by a synthetic restriction fragment having the corresponding base sequence except for a mutation in the middle. Substitution, deletion, addition or transposition may be made in DNA by the technique called the site-specific mutagenesis (Kramer, W. and Frits, H. J., Meth. in Enzymol., 154, 350 (1987); Kunkel, T. A. et al., Meth. in Enzymol., 154, 367 (1987)). The enzyme activity is measured by known methods (J. Biol. Chem., 267, 22711–22714 (1992)), and it will be easy for those skilled in the art to select nucleotides to substitute, delete, add or transpose to make a mutant DNA encoding an amino acid sequence containing substitution, deletion, addition or transposition of at least one amino acid residues which substantially does not impair the activity based on the desired enzyme activity.

Further, those skilled in the art should easily understand that the DNA of the present invention also includes DNA having different base sequences due to degeneracy of the genetic code.

The genomic GlcAT-P gene is presumed to have an intron in the coding region, and the DNA of the present invention also include such DNAs interrupted by introns as long as the DNAs encode at least part of the amino acid sequence of GlcAT-P. Namely, in the present specification, "encode" also means a base sequence which will give the polypeptide of interest after processing during transcription.

In the present specification, "encode at least part of the polypeptide" means preferably a region having some kinds activities or functions such as a GlcAT-P activity or immunogenicity or a region having a base sequence so peculiar to GlcAT-P to be used for a primer or a probe.

The DNA of the present invention also includes DNAs or RNAs which are complementary to the DNA of the present invention. The DNA of the present invention may be a single coding strand encoding GlcAT-P, or may be composed of two strands; one of which is the coding strand, and the other is a DNA or RNA strand complementary to the coding strand.

The DNA of the present invention may have a base sequence encoding all or part of the polypeptide of GlcAT-P.

The method of preparing the DNA of the present invention is explained below. Since the amino acid sequence encoded by the base sequence of the DNA of the present invention is identified by way of the present invention, the DNA of the present invention can be obtained as a PCR (polymerase chain reaction) product of a genetic DNA or a mRNA by using synthetic oligonucleotide primers based on the sequence, and is also obtainable by the cDNA cloning comprising the following steps.

(1) Determination of the amino acid sequence of at least part of the polypeptide of isolated GlcAT-P, (2) Synthesis of oligonucleotide primers based on the amino acid sequence, (3) Preparation of a probe for the transferase by amplification of cDNA prepared from RNA extracted from a mammal tissue by PCR using the primers, and (4) Screening of a cDNA library derived from the mammal tissue by using the probe, usually to select a full-length cDNA of the transferase.

However, there is no imitation on preparation of the DNA of the present invention, and the DNA of the present invention is also obtainable not only by the above-mentioned PCR but also other known techniques for cDNA cloning.

A method for preparing the DNA of the present invention is explained in detail below.

(1) Determination of the amino acid sequence of glucuronyltransferase-P (GlcAT-P)

(i) Isolation of GlcAT-P

GlcAT-P can be isolated from cells in tissues expressing GlcAT-P such as the brain, of mammals such as human, rat, mouse, cattle, pig, horse, cat and dog, preferably from the rat brain, by a conventional procedure for extraction of proteins combined with affinity chromatography using a substrate of GlcAT-P (such as uridine diphosphate (UDP)-glucuronic acid) or an inhibitor (such as the above-mentioned glycolipid inhibitor). Specifically, the isolation can be accomplished by the method disclosed in J. Biol. Chem., 267, (32), 22711–22714 (1992).

(ii) Determination of the partial amino acid sequence of GlcAT-P

The method for fragmentation of the isolated GlcAT-P is not particularly limited, and the protein can be fragmented by known methods such as incubation with a protease such as trypsin. Treatment of the GlcAT-P with trypsin may be followed by fractionation by high pressure liquid chromatography (HPLC). The peptides produced after the protease degradation can be sequenced from the amino-terminals by known methods. Particularly, use of model 476A protein sequencer (Applied Biosystems) is preferred for the sequencing, but this is not the only approach. Sequencing services are also available.

(iii) Synthesis of oligonucleotide primers

On the basis of a partial amino acid sequence of GlcAT-P, oligonucleotide primers are synthesized. Partial amino acid sequences which are encoded with the minimum codon degeneracy are preferably used to design the oligonucleotide primers. Example of such degenerated oligonucleotide primers are given in FIG. 1 (sense primers: SEQ ID NOS: 6, 9 and 10; antisense primers: SEQ ID NOS: 7, 8 and 11).

(2) Preparation of a partial GlcAT-P cDNA and a probe

① mRNA is obtainable by known methods (Kingston, R. S., (1991) in Current Protocols in Molecular Biology, Suppl. 14, Unit 4.2, Greene Publishing Associates and Wiley Interscience, New York). The mRNA source is not particularly limited as long as it expresses GlcAT-P mRNA, but mammal tissues as mentioned above, particularly the cerebral cortex of rats are preferred. The cerebral cortex of about 2-week old rats, which expresses the mRNA of the enzyme strongly, is particularly preferred.

The total RNA is obtainable from the above-mentioned source by a usual mRNA preparation method, preferably by the guanidinethiocyanate/CsCl method (Kingston, R. B., (1991) in Current Protocols in Molecular Biology, Suppl. 14, Unit 4.2, Greene Publishing Associates and Wiley Interscience, New York) or the guanidiumthiocyanate-phenol-chloroform method (Chomczynski, P. and Sacchi, N., Anal. Biochem., 162, 156–159 (1987)) for the sake of convenience.

② Preparation of the amplified partial GlcAT-P cDNA by reverse transcription and PCR The DNA product of reverse transcription of mRNA with a random primer or an oligo dT primer is used as the template DNA for PCR which yields an amplified partial GlcAT-P cDNA. The reverse transcription can be carried out in an ordinary method, specifically by incubating 20 $\mu$g of mRNA, 40 pmol of a random primer or an oligo dT primer, 500 $\mu$M of each of the four deoxynucleoside triphosphates, 200 units of M-MLV reverse transcriptase (Gibco BRL), 10 mM of dithiothreitol (DTT) and 30 units of human placental ribonuclease (RNase) inhibitor in a buffer solution (total volume 40$\mu$) at 42° C. for 1 hour. The reverse transcription product is used for PCR with the above-mentioned degenerate oligonucleotide primers in a reaction solution containing 2 $\mu$l of the reverse transcription product (corresponding to 1 $\mu$g of mRNA), 100 pmol of degenerate oligonucleotide primers, 500 $\mu$M of each of the deoxynucleoside triphosphates and 1.25 units of Taq polymerase by 35 cycles of 94° C. for 30 sec, 45° C. for 60 sec, and 72° C. for 90 sec. Then the PCR product is used for another round of PCR with oligonucleotide primers corresponding to inner portions of the degenerate oligonucleotide primers by 20 cycles of 94° C. for 30 sec, 45° C. for 60 sec, and 72° C. for 90 sec. The PCR product is subcloned into an appropriate plasmid such as pCRII and its base sequence is determined by a conventionally known method. Based on the base sequence, among the degenerate oligonucleotide primers, only those completely matched are synthesized and used for PCR. Amplification proceeds in a reaction solution (total volume 25 μl) containing 1 μl of the reverse transcription product, 20 pmol of the completely matched oligonucleotide primers, 500 μM of each of the deoxynucleoside triphosphates and 1.25 units of Taq polymerase by 35 cycles of 94° C. for 30 sec, 45° C. for 60 sec, and 72° C. for 90 sec. The resulting partial cDNA is used as a probe for screening a cDNA library by hybridization to identify the full-length cDNA (a cDNA containing the entire coding region). The partial cDNA used as a hybridization probe may be labeled with [$^{32}$P]dCTP during amplification, for example, by the random primer label method so as to serve as a radioactive probe in the cDNA library screening.

(3) Construction of a cDNA library (i) Preparation of cDNA and recombinant DNA

A cDNA is obtained by a usual method for reverse transcription of template mRNA. Commercial cDNA preparation kits may be used for the sake of convenience. For example, Time Saver cDNA synthesis kit (Pharmacia LKB biotechnology) facilitates preparation of cDNA joined with a cloning vector. A commercially available cDNA library may be used for the sake of convenience. In the present invention, a λgt11 cDNA library constructed from the mRNA obtained from the brain of embryonic day 18 SD rats (CLONTECH) is used. Recombinant cloning vector DNA containing cDNA inserts is introduced into host bacterial cells (transfection). The host bacterium should be chosen depending on the cloning vector, and the combination of a cloning vector which assigns *Escherichia coli* (*E. coli*) as a host and *E. coli* is usually used, but other combinations may be used. For the transfection, 30 mM calcium chloride-treated *E. coli* cells having an altered cell membrane permeability are usually mixed with the recombinant DNA. When A phage vectors such as λgt11 and Lamda ZAP are used, the recombinant DNA can directly be introduced into calcium chloride-treated *E. coli* cells, but the recombinant vector DNA is usually packed in phage particles in vitro (in vitro packaging) before introduction into *E. coli* cells for the sake of efficient transfection, and commercially available packaging kits (such as Gigapack II packaging extract, Stratagene) may be used for the packaging. The packed recombinant DNA is transfected into *E. coli*. The E. coil strain should be selected depending on the cloning vector used. Namely, *E. coli* strains resistant to antibiotics can not be used for cloning vectors containing an antibiotic resistant gene, and *E. coli* strains which do not exhibit β-galactosidase activity should be selected for cloning vectors containing β-galactosidase gene (lacZ). Such selection is necessary for screening *E. coli* cells transfected with the recombinant DNA. For example, *E. coli* strains such as *E. coli* Y1090$^{r-}$ and *E. coli* XL-1 Blue may be selected for λgt11 and Lamda ZAP cloning vectors. *E. coli* cells carrying recombinant DNA or a recombinant plasmide can be identified because they have acquired antibiotic resistance or β-galactosidase activity. In actual procedure, *E. coli* cells are plated on an agar medium so as to selectively form colonies The surviving *E. coli* cells (which are transfected with recombinant DNA) constitute a cDNA library. When bluescript is used as a plasmide, host cells suspended in a soft agar medium with the plasmide are plated on an agar medium so as to form colonies. Colonies which contain the plasmide containing a DNA insert do not show β-galactosidase activity and therefore can easily be identified.

(ii) Screening for the full-length GlcAT-P cDNA

From the cDNA library thus obtained, clones containing the full-length GlcAT-P cDNA can be selected by hybridization using a partial GlcAT-P cDNA probe. The screening procedure is easy and comprises blotting *E. coli* colonies carrying the plasmide onto a nitrocellulose or nylon membrane and hybridizing the resulting replicas of the colonies on the membrane with the partial cDNA probe. The phage DNA is isolated from clones identified as positive and cut down by an appropriate restriction enzyme to give the GlcAT-P cDNA.

(iii) Determination of the base sequence of the GlcAT-P cDNA

The DNA fragments prepared by PCR as mentioned above using various oligonucleotide primers and an oligo dT primer and the cDNA obtained by the above-mentioned cloning procedure are sequenced by conventionally known methods directly or after subcloned into appropriate plasmides such as pCRII.

The base sequence of the GlcAT-P cDNA and the amino acid sequence deduced from the base sequence are shown in SEQ ID NO:1, and the amino acid sequence only is shown in SEQ ID NO:2.

A DNA encoding the polypeptide of a soluble form of GlcAT-P is prepared according to the following procedure. First, primers designed for production of an appropriate N-terminal truncated form of the polypeptide on the basis of the base sequence shown in SEQ ID NO:1 are synthesized and used for amplification of the cloned GlcAT-P cDNA by PCR. For example, a DNA encoding a truncated form of GlcAT-P lacking the N-terminal 74 residues can be obtained by PCR using primers having the base sequences shown in SEQ ID NOS:19 and 20 as the 5' and 3' primers, respectively. The DNA fragment of interest is isolated from the PCR product, if necessary.

<2> The method of producing the polypeptide of GlcAT-P using the DNA of the present invention Cells transformed with the DNA of the present invention are grown in an appropriate medium so as to produce the polypeptide encoded by the DNA of the present invention in the culture, and the polypeptide of the GlcAT-P of the present invention is isolated from the culture.

Cells transformed with the DNA of the present invention are obtained by inserting the DNA fragment of the present invention into a plasmide expression vector and introducing the recombinant plasmide into cells of procaryotes such as *E. coli* or eucaryotes such as mammals.

A recombinant plasmid is prepared, for example, by the procedure described below. The DNA of the present invention is inserted between the EcoRI-BamHI sites of pGIR201protA (Kitagawa, H. and Paulson, J. C., J. Biol. Chem., 269, 1394–1401 (1994)) by a conventional method so that the GlcAT-P fused with insulin signal sequence and the protein A is encoded in the reading frame of the resulting vector. Then, the NheI fragment encoding the fusion protein is cut out of the vector and inserted into the XbaI site of pEF-BOS (Mizushima, S. and Nagata, S., Nucleic Acids Res., 18, 5322 (1990)) in the same manner as described above.

In the method of the present invention, ordinary host-vector systems used for production of proteins can be used, and the combination of mammalian cells such as COS-1 cells with a mammalian expression vector for such as pEF-BOS is preferred. The culture medium and the incubation conditions should be selected depending on the cells to be used as the host.

The DNA of the present invention may be expressed solely or in the form of a fused polypeptide with other polypeptides, and may be expressed entirely or partially as a partial peptide. The present invention covers DNAs expressed as such partial polypeptides and methods for expressing such DNAs.

The polypeptide is recovered from the culture by a known method for purifying polypeptides, such as affinity chromatography using an asialoorosomucoid- or UDP-glucuronic acid-conjugated Sepharose column. The culture contains the medium and the cells.

The GlcAT-P and its fusion form thus obtained enable mass production of the HNK-1 antigen. The HNK-1 antigen thus produced can, for example, be used medically as a diagnostic medicine for peripheral neuropathy attributable to autoimmune disease, which is known to induce increase of the level of antibodies against the antigen in the blood. Namely, peripheral neuropathy can be diagnosed practically from the amount of antibodies bound to the antigen. GlcAT-P, its fused forms and cells transformed with the DNA of the present invention can be used for research purposes as reagents to elucidate the association of the HNK-1 antigen with the development of the nervous system, the mechanism of the immune system and the functions of GlcAT-P in vivo.

Now, the present invention will be described in further details by referring to Examples, but the present invention should not be restricted to these specific Examples.

<1> Isolation of the rat GlcAT-P and analysis of the amino acid sequence

GlcAT-P was purified by affinity chromatography using a UDP-glucuronic acid-conjugated Sepharose column by the method disclosed in J. Biol. Chem., 267, 22711–22714. GlcAT-P was eluted with 10 mM HEPES buffer (pH 6.5) containing 0.4% (v/v) Nonidet P-40 (trade name), 1 M NaCl and 10 mM EDTA by the affinity chromatography using the UDP-glucuronic acid-conjugated Sepharose column under the conditions disclosed in the paper.

The purified GlcAT-P was degraded with trypsin in 50 mM Tris-HCl buffer, pH 9.0, at 37° C. overnight. The degradation product was filtered and lyophilized. The lyophilized product was subjected to HPLC using a reverse phase column (2.1×150 mm) after dissolved in 18 µl of the mobile phase A (0.06% (V/V) trifluoroacetic acid (TFA) containing 1% (V/V) acetonitrile). Peptides were eluted with a concentration gradient of from 2% to 100% of mobile phase B (80% (V/V) acetonitrile containing 0.052% (V/V) TFA) in mobile phase A over 100 minutes at a flow rate of 3.3 µl/min. The absorbance at 214 nm was monitored, and the peptide fractions were collected manually and subjected to amino acid sequencing by model 476A protein sequencer (Applied Biosystems). The results are shown in Table 1. The underlined amino acid sequences were used as the basis for synthesis of degenerate oligonucleotide primers. The amino acids printed in lowercase letters are those which were not identified clearly.

TABLE 1

| Peptide No. | Amino acid sequence | SEQ ID NO: |
|---|---|---|
| 1 | MANTLLH<u>VPNLHWL</u>VVEDAPR | 3 |
| 2 | STQPGVV<u>YFADDDNTY</u>sLELFEEMs | 4 |
| 3 | TVFDPHvPFAID<u>MAGFA</u>VNLgr | 5 |

<2> Amplification of a partial GlcAT-P cDNA by PCR (1) Synthesis of PCR primers

The terminal and inner degenerate oligonucleotide primers containing deoxyinosine as shown in FIG. 1 were synthesized on the basis of the underlined amino acid sequences of peptides 1, 2 and 3 (template DNA primers Pr.1-s (SEQ ID NO:6), Pr.2-so (SEQ ID NO:9) and Pr.2-si (SEQ ID NO:10), and complementary primers Pr.1-ao (SEQ ID NO:7), Pr.1-ai (SEQ ID NO:8) and Pr.2-a (SEQ ID NO:11)).

(2) PCR

A single-stranded cDNA (total volume 40 µl) was prepared by using random primers and the total RNA (20 µg) isolated from the cerebral cortex of 2-week-old rats by the guanidinethiocyanate-phenol-chloroform method as a template, and the reverse transcription product was used as a template for subsequent PCR. Amplification proceeded in 25 µl of a PCR solution containing 2 µl of the reverse transcription product, 100 pmol of a pair of terminal primers pr.1-s and pr.1-ao (or pr.2-so and pr.2-a), 500 µM of each of the four deoxynucleoside triphosphates and 1.25 U of AmpliTaq polymerase (Perkin Elmer) by 35 cycles of denaturation at 94° C. for 30 sec, annealing at 45° C. for 60 sec and elongation at 72° C. for 90 sec. 1 µl aliquots of the amplification products were subjected to 20 cycles of PCR at 94° C. for 30 sec, at 45° C. for 60 sec and at 72° C. for 90 sec with a pair of primers pr.1-s and pr.1-ai (or pr.2-si and pr.2-a). Analysis of the amplification products by conventional agarose gel electrophoresis detected a band of about 260 bp (A1) for pr.1-s and pr.1-ai and a band of about 210 bp (A2) for pr.2-si and pr.2-a.

<3> Full-length GlcAT-P cDNA (1) Synthesis of a hybridization probe

The amplification products A1 and A2 were subcloned into pCRII (Invitrogen) by a conventional method, and their base sequences were analyzed with ABI PRISM Dye terminator Cycle Sequencing Ready Reaction kit (PERKIN ELMER). On the basis of the results of the sequence analysis, an oligonucleotide adjacent to the primer pr.1-s used for preparation of the amplification product A1 (pr.a (SEQ ID NO:12)) and an oligonucleotide adjacent to the primer pr.2-si used for preparation of the amplification product A2 (pr.b (SEQ ID NO:13)) were synthesized. 35 cycles of PCR at 94° C. for 30 sec, 47° C. for 60 sec and at 72° C. for 50 sec was carried out in a total volume of 25 µl of solution containing 20 pmol of pr.a and pr.b, 2 µl of the reverse transcription product and 500 µM of each of the four deoxynucleoside triphosphates to give an amplification product (gf.a). The amplification product gf.a was subcloned into pCRII and sequenced (SEQ ID NO:16). The plasmide was prepared in a large amount and degraded with EcoRI to give a large amount of gf.a, which was used for the subsequent screening.

(2) Screening for GlcAT-P cDNA clone

A λgt11 cDNA library constructed from the mRNA obtained from the brain of embryonic day 18 SD rats was purchased from Clonetec Inc., and transfected into host cells E. coli Y1090$^{r-}$, and the host cells were plated to form about 5×10$^5$ plaques on 10 dishes of 150 mm. The plaques were then screened. The plaques were transferred to OPTITRAN BA-S 85 nitrocellulose membranes (Schleicher & Schuell), then crosslinked with UV light, incubated in 50 mM phosphate buffer, pH 7.0, containing 50% formamide, 5×SSC (sodium chloride/sodium citrate), 0.5% of skim milk, 0.1% of SDS and 100 µg/ml of yeast tRNA at 42° C. for 16 hours preliminarily, and then incubated with $^{32}$P-labeled gf.a added to the buffer at 42° C. for 16 hours for hybridization.

The membranes were washed with 2×SSC, 0.5% SDS at room temperature, with 1×SSC, 0.1% SDS at 65° C. and with 0.2×SSC at 65° C. 17 clones were identified as positive by autoradiography, and eight of them were isolated.

(3) Base Sequence of GlcAT-P cDNA clones

The phage DNA was isolated from the eight clones, and the cDNA insert fragment was prepared from the vector DNA by PCR. The nucleotide sequence of each strand of the cDNA fragment was determined independently by the deoxy chain termination method (Sanger, F., Nicklens, S., and Coulson, A. R. (1977) Proc. Natl. Acad. Sci. U.S.A. 74, 5463–5467) using ABI PRISM Dye terminator Cycle Sequencing Ready Reaction kit (PERKIN ELMER) using the cDNA fragment as the template, and the base sequence of the common region gf.b was identified (SEQ ID NO:17).

(4) Preparation of the 5'-terminal region of the GlcAT-P cDNA and determination of its base sequence Since gf.b lacked the 5'-terminal region judging from its base sequence, the 5'-terminal region of the cDNA was prepared directly from the mRNA isolated from the cerebral cortex of 2-week-old rats. A cDNA was prepared by reverse transcription with pr.b and polyadenylation at the 3'-end with terminal doxytransferase. The reverse transcription product was amplified by PCR using oligo (dT)-primer and pr.c-1 (SEQ ID NO:14) under the same conditions as above and then amplified again by PCR with oligo (dT)-primer and pr.c-2 (SEQ ID NO:15) to yield a DNA fragment of about 600 bp (gf.c (SEQ ID No:18)). The fragment gf.c was amplified by a conventional method and then subcloned into pCRII (Invitrogen), and the nucleotide sequence of each strand as determined independently in the same manner as described above.

(5) Determination of the complete base sequence of GlcAT-P cDNA

From the overwrapping base sequences of gf.b and gf.c, the complete base sequence of GlcAT-P cDNA was determined. FIG. 2 indicates the locations of fragments gf.a, gf.b and gf.c and the primer sequences.

The amino acid sequence deduced from the base sequence of the GlcAT-P cDNA thus determined (SEQ ID NO:1) is shown in SEQ ID NO:2. The cDNA contains an open reading frame encoding a polypeptide of 347 amino acid residues having a predicted molecular weight of 39706 with three potential N-glycosylation sites. Hydropathy analysis of the deduced amino acid sequence was done to show if the polypeptide has transmembrane domains and if any, where they are. The hydropathy analysis was done by the method of Hopp and Woods (Hopp, T. P. and Woods, K. R., Proc. Natl. Acad. Sci. USA, 78, 3824–3828 (1981)) with 5 amino acid residues in a window and indicated one distinguishing hydrophobic region of 17 residues long near the amino-terminal, as a putative transmembrane domain. This indicates that the polypeptide is a type II transmembrane protein having the N-terminal region of 19 amino acid residue long preceding the transmembrane domain.

(6) Nothern blotting

Total RNA was extracted by the guanidiumthiocyanate-phenol-chloroform method described in Anal. Biochem. 162, 156–159 from adult rat tissues (the cerebral cortex, cerebellum, whole brain, lung, liver, kidney, ileum, testis, lymphoid nodule, thymus, spleen, heart and macrophages). Equal amounts of the RNA extracts (10 µg each lane) were fractionated by electrophoresis according to size in 1% agarose-formaldehyde gel and blotted onto Hybond N+ nylon membranes (Amersham). The blot was hybridized with $^{32}$P-labeled GlcAT-P cDNA at 65° C. for 14 hours in 0.5 M NaH$_2$PO$_4$ (pH 7.2) containing 7% SDS, 1 mM EDTA and 1% Bovine Serum Albumin (BSA), and washed with 2×SSC, 1% SDS at room temperature, with 0.2×SSC, 0.1% SDS at 65° C. and with 0.1% SDS, 0.1×SSC at 65° C. The radioactivity was visualized by an image analyzer (Bas 2000, Fuji Photo Film), and RNA transcripts of GlcAT-P (major transcript of 4.0 kb and minor transcript of 9.1 kb) were detected in the cerebral cortex, cerebellum and whole brain, but not in peripheral tissues such as the liver and kidney.

(7) Construction of an expression vector

A DNA fragment having a base sequence of SEQ ID NO:1 was prepared by reverse transcription of mRNA from the brain of 2-week-old rats followed by amplification of the resulting single-stranded DNA by PCR using a 5'-primer and a 3'-primer containing a BamHI site 18 bp downstream of the stop codon. The DNA fragment was blunted by a known method and then joined with a mammalian vector pEF-BOS (provided by Nagata, S. (Osaka Bioscience Institute)) which had been degraded with BstXI, blunted and dephosphorylated, by a known method.

(8) Construction of an expression vector containing the cDNA of a soluble form of GlcAT-P A DNA encoding a truncated form of GlcAT-P lacking the first 74 amino acid residues which cover the transmembrane domain of GlcAT-P was prepared by amplifying the cloned GlcAT-P cDNA as the template by PCR using a 5'-primer containing an in-frame EcoRI site (SEQ ID NO:19) and a 3'-primer (SEQ ID NO:20). The resulting DNA fragment was inserted between the EcoRI-BamHI sites of pGIR201protA (Kitagawa, H: and Paulson, J. C. , J. Biol. Chem., 269, 1394–1401 (1994)) by an ordinary method in order to construct a vector having an open reading frame encoding GlcAT-P, insulin signal sequence and protein A fused into one protein. A clone containing the correct sequence was selected, and the NheI fragment containing the fusion protein was inserted into the XbaI site of pEF-BOS (Mizushima, S. and Nagata, S., Nucleic Acids Res., 18, 5322 (1990)) in the same manner as described for construction of the above-mentioned expression vector.

(9) Transient expression of a soluble form of GlcAT-P in COS-1 cells

COS-1 cells (ATCC: CRL-1650) were grown on tissue culture dishes (100 mm) for 24 hours and then transfected with 8.2 µg of the expression vector pEF-BOS containing the cDNA of a soluble form of GlcAT-P by using Lipofect AMINE (Life Technologies). After five days, the supernatant of the cell culture was recovered and the GlcAT-P activity was measured by using asialoorosomucoid as the glucuronic acid acceptor according to the method disclosed in J. Biol. Chem., 267, 22711–22714 (1992). For comparison, COS-1 cells were transfected with empty pEF-BOS vector and the supernatant of the culture was recovered. The results are shown in Table 2.

TABLE 2

|  | Transfection | Mock |
| --- | --- | --- |
| Enzyme activity | 70 µunit/ml | <0.7 µunit/ml |

The soluble form of GlcAT-P in the culture was isolated by using an asialoorosomucoid-conjugated Sepharose column. Although normal GlcAT-P has Cys-70 and Cys-317, the purified soluble form of GlcAT-P retains Cys-317 only. The results that the soluble form of GlcAT-P has activity and that the soluble form lost its activity when exposed to the SH-blocking agent, N-ethylmaleimide indicate that the two cysteine residues do not form a disulfide bond and the SH group of Cys-317 is associated with the activity of the enzyme.

(10) Transient expression of GlcAT-P in Lec 2 cells

Lec 2 cells (ATCC: CRL-1736), which is a mutant cell line derived from CHO cells and has glycoproteins having N-acetyllactosamine residues as glucuronic acid acceptors, were transfected with pEF-BOS vector containing the full-length GlcAT-P cDNA. The Lec 2 cell line lacks the CMP-sialic acid transport system and expresses glycoproteins having N-acetyllactosamine residues without terminal sialic acid on the surface. Therefore, Lec 2 is thought to closely reflect the physiological activity of GlcAT-P, because there is no possibility of competitive between transfer of glucuronic acid to the N-lactosamine structure by GlcAT-P and transfer of sialic acid by any endogenic enzymes. Lec 2 cells were grown on tissue culture dishes (60 mm) for 24 hours and transfected with 3 µg of pEF-BOS vector containing the full-length GlcAT-P cDNA or mock empty pEF-BOS vector by using Lipofect AMINE (Life Technologies). After 72 hours, the cells were collected in PBS containing 1 mM EDTA and incubated with an anti-paragloboside antibody, H11 (provided by Taki, T. (Tokyo Medical and Dental University)), M6749, which recognizes glucuronic acid residues in the HNK-1 epitope (provided by Tanaka, H., (Kumamoto University)), the HNK-1 antibody (ATCC: TIB-200) which recognizes sulfated glucuronic acid, and a control mouse IgM as primary antibodies at 4° C. for 1 hour. Cells were washed with PBS buffer containing EDTA and incubated with a FITC-conjugated anti-mouse IgM antibody as the secondary antibody and analyzed by FACS. The results are shown in FIG. 3. The staining profile of H11 antibody does not change before and after transfection with the full-length GlcAT-P cDNA, suggesting that GlcAT-P does not transfer glucuronic acid to a glycolipid acceptor, paragloboside. The fact that the transfected cells were not stained by HNK-1 indicates that Lec 2 cells lack the enzyme that sulfates the transferred glucuronic acid. The fact that the cells were stained with M6749 more strongly after transfection indicates that the GlcAT encoded by the cDNA transfers glucuronic acid like normal GlcAT does.

(11) Transient expression of GlcAT-P in COS-1 cells

COS-1 cells were grown on tissue culture dishes (60 mm) precoated with laminin for 24 hours and transfected with 3 µg of pEF-BOS vector containing the full-length GlcAT-P cDNA or an equal amount of the empty vector pEF-BOS as the mock by using Lipofect AMINE (Life Technologies). After 72 hours, the transfected cells were fixed with 3% paraformaldehyde in PBS, incubated with 10 µg/ml M6749 or HNK-1 for 2 hours at room temperature, then visualized with FITC-conjugated anti-mouse IgM antibody. The cells transfected with the GlcAT-P cDNA were stained with M6749 and HNK-1, whereas the mock-transfected cells were not. The COS-1 cells expressing the GlcAT-P cDNA exhibited dramatic morphological changes, as compared with a mock-transfected cells, and expended long processes with a number of microspikes.

The present invention provides a DNA having a base sequence encoding glucuronyltransferase-P (GlcAT-P), which selectively transfers glucuronic acid to lactosamine residues of glycoproteins. The DNA having a base sequence encoding GlcAT-P according to the present invention is expected to enable GlcAT-P to be produced in a large amount enough for industrial use. Use of the DNA of the present invention enables production of a soluble form of the enzyme having the same activity as that on the cell membrane, and facilitates synthesis of the HNK-1 epitope using the enzyme and elucidation of the functions of the enzyme in living organisms.

What is claimed is:

1. An isolated DNA encoding at least part of a glucuronyltransferase polypeptide consisting of amino acids 1 to 347 in SEQ ID NO:2, wherein the DNA encoding a polypeptide that is capable of transferring glucuronic acid from a glucuronic acid donor to glucuronic acid acceptor.

2. An isolated DNA encoding at least part of a glucuronyltransferase polypeptide consisting of amino acids 75 to 347 in SEQ ID NO:2, wherein the DNA encoding a polypeptide that is capable of transferring glucuronic acid from a glucuronic acid donor to glucuronic acid acceptor.

3. An isolated DNA molecule encoding a rat glucuronyltransferase wherein said glucuronyltransferase:

A) is capable of transferring glucuronic acid from a glucuronic acid donor to a glucuronic acid acceptor;
   B) is capable of selectively transferring of glucuronic acid to N-acetyllatosamine residue of asialoorosmucoid and neural cell adhesion molecule;
   C) has an optimum pH of about 6.0 to 6.5 (in 100 mM MES buffer at 37° C.);
   D) is activated by $Mn^{2+}$ and the activity is maintained in the presence of 5 mM of neolactotetrasose-phenyl-$C_{14}H_{29}$; and
   E) has a molecular weight of about 45,000 Daltons measured by reductive SDS-polyacrylamide gel electrophoresis and a molecular weight of about 90,000 Daltons measured by gel filtration.

4. An isolated DNA encoding at least part of a mammalian glucuronyltransferase polypeptide, wherein said glucuronyltransferase polypeptide consists of an amino acid sequence SEQ ID NO:2, wherein a substitution, deletion, addition or transposition of at least one amino acid residue is made in SEQ ID NO:2 to produce a mutant polypeptide, such that said mutant polypeptide can transfer glucuronic acid from a glucuronic acid donor to asialoorosmucoid being a glucuronic acid acceptor.

5. An isolated DNA molecule comprising SEQ ID NO:1, encoding rat glucuronyltransferase.

6. A plasmid vector containing the isolated DNA of claim 5.

7. A prokaryotic or eukaryotic cell containing the isolated DNA of claim 5.

8. A method of producing a polypeptide, which comprises culturing cells transformed with the DNA according to claim 5 in an appropriate culture medium, allowing the cells to produce and accumulate the glucuronyltransferase polypeptide encoded by the base sequence of the DNA in the cultured cells, and isolating the polypeptide from the cultured cells and culture medium.

9. The DNA molecule of claim 10 encoding rat glucuronyltransferase-P.

10. An isolated DNA which hybridizes to a polynucleotide complementary to SEQ ID NO:1 under the following conditions:
   (a) hybridization at 65° C. for 14 hours in a solution containing 0.5M $NaH_2PO_4$ (pH 7.2), 7% SDS, 1 mM EDTA and 1% bovine serum albumin;
   (b) washing in 2×SSC, 1% SDS at room temperature;
   (c) washing in 0.2×SSC, 0.1% SDS at 65° C.; and
   (d) washing in 0.1×SSC, 0.1% SDS at 65° C. wherein the DNA encodes a polypeptide that is capable of transferring glucuronic acid from a glucuronic acid donor to glucuronic acid acceptor.

11. The isolated DNA according to claim 10, wherein said DNA hybridizes to a polynucleotide complementary to nucleotides 195–1235 of SEQ ID NO:1.

12. The isolated DNA according to claim 10, wherein said DNA hybridizes with a polynucleotide complementary to the nucleotides of SEQ ID NO:1 which encode amino acids 75 to 347 of SEQ ID NO:2.

13. A plasmid vector containing the isolated DNA of claim 10.

14. A prokaryotic or eukaryotic cell containing the isolated DNA of claim 10.

15. A method of producing a polypeptide, which comprises culturing cells transformed with the DNA, according to claim 10, in an appropriate culture medium, allowing the cells to produce and accumulate the glucuronyltransferase polypeptide encoded by the base sequence of the DNA in the cultured cells, and isolating the polypeptide from the cultured cells and culture medium.

* * * * *

SEQUENCE LISTING

```
(1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 2090 base pairs
        (B) TYPE: nucleic acid
        (C) STRANDEDNESS: both
        (D) TOPOLOGY: linear (ii) MOLECULE TYPE: cDNA (vi) ORIGINAL SOURCE:
        (A) ORGANISM: WISTAR RAT
        (F) TISSUE TYPE: CEREBRAL CORTEX (ix) FEATURE:
        (A) NAME/KEY: CDS
        (B) LOCATION: 195..1235
        (D) OTHER INFORMATION: /note= "DEFINE METHOD: P"

(ix) FEATURE:
        (A) NAME/KEY: misc_feature
        (B) LOCATION: 252..302
        (D) OTHER INFORMATION: /note= "TRANSMEMBRANE DOMAIN,
            DEFINE METHOD"

(ix) FEATURE:
        (A) NAME/KEY: misc_feature
        (B) LOCATION: 651..659
        (D) OTHER INFORMATION: /note= "POTENTIAL N-GLYCOSYLATION
```

```
                SITE, DEFINE METHOD: S"

(ix) FEATURE:
         (A) NAME/KEY: misc_feature
         (B) LOCATION: 783..791
         (D) OTHER INFORMATION: /note= "POTENTIAL GLYCOSYLATION
                SITE, DEFINE METHOD: S"

(ix) FEATURE:
         (A) NAME/KEY: misc_feature
         (B) LOCATION: 1140..1148
         (D) OTHER INFORMATION: /note= "POTENTIAL N-GLYCOSYLATION
                SITE, DEFINE METHOD: S"

(xi) SEQUENCE DESCRIPTION: SEQ ID NO:1:

GCGCGCGCAT CGCAGGGCAG CAGCCCTGGG TCTCTGGGGC CAGGGCATAG GACTGCCACC        60

CGCTATGGAC CGCGCCAGGG ACGATATGGA CTCGCTGCCG CAGGTATCAA CCTCCGAAGG       120

TTCCTGACCC TGCGCTGGAC TACTTCCCCT TCGCAGACTC CCATCAGGCC GGACTCTGCA       180

AACCTGCTGC CACA ATG GGT AAT GAG GAG CTG TGG GCG CAG CCA GCC TTG         230
              Met Gly Asn Glu Glu Leu Trp Ala Gln Pro Ala Leu
                1               5                  10

GAG ATG CCG AAG AGA AGG GAC ATC CTC GCG ATT GTC CTC ATT GTG CTT         278
Glu Met Pro Lys Arg Arg Asp Ile Leu Ala Ile Val Leu Ile Val Leu
              15                  20                  25

CCC TGG ACA CTG CTC ATC ACC GTC TGG CAC CAG AGC AGC CTC GCA CCT         326
Pro Trp Thr Leu Leu Ile Thr Val Trp His Gln Ser Ser Leu Ala Pro
         30                  35                  40

CTG CTT GCT GTG CAC AAG GAT GAG GGA AGT GAC CCC CGC CAT GAG GCA         374
Leu Leu Ala Val His Lys Asp Glu Gly Ser Asp Pro Arg His Glu Ala
 45                  50                  55                  60

CCA CCC GGT GCG GAC CCT AGG GAG TAC TGC ATG TCC GAC CGT GAC ATC         422
Pro Pro Gly Ala Asp Pro Arg Glu Tyr Cys Met Ser Asp Arg Asp Ile
                  65                  70                  75

GTG GAG GTG GTG CGC ACA GAG TAC GTG TAC ACG AGG CCG CCA CCG TGG         470
Val Glu Val Val Arg Thr Glu Tyr Val Tyr Thr Arg Pro Pro Pro Trp
             80                  85                  90

TCC GAC ACG CTG CCC ACC ATC CAT GTG GTG ACG CCC ACC TAC AGT AGA         518
Ser Asp Thr Leu Pro Thr Ile His Val Val Thr Pro Thr Tyr Ser Arg
         95                  100                 105

CCG GTG CAG AAG GCA GAG CTG ACG CGA ATG GCC AAC ACG CTA TTG CAT         566
Pro Val Gln Lys Ala Glu Leu Thr Arg Met Ala Asn Thr Leu Leu His
     110                 115                 120

GTG CCC AAC CTT CAC TGG CTG GTG GTG GAG GAT GCT CCA CGT AGG ACG         614
Val Pro Asn Leu His Trp Leu Val Val Glu Asp Ala Pro Arg Arg Thr
125                 130                 135                 140

CCC CTC ACA GCG CGC CTG CTG CGC GAC ACT GGC CTC AAC TAT ACA CAC         662
Pro Leu Thr Ala Arg Leu Leu Arg Asp Thr Gly Leu Asn Tyr Thr His
                145                 150                 155

CTG CAC GTA GAG ACA CCA CGC AAC TAC AAG CTG CGA GGT GAC GCC CGA         710
Leu His Val Glu Thr Pro Arg Asn Tyr Lys Leu Arg Gly Asp Ala Arg
                160                 165                 170

GAC CCT CGC ATC CCA CGT GGC ACC ATG CAG CGC AAT CTG GCC CTG CGC         758
Asp Pro Arg Ile Pro Arg Gly Thr Met Gln Arg Asn Leu Ala Leu Arg
         175                 180                 185

TGG TTG CGG GAG ACC TTC CCA CGG AAC TCC ACT CAG CCG GGT GTA GTG         806
Trp Leu Arg Glu Thr Phe Pro Arg Asn Ser Thr Gln Pro Gly Val Val
     190                 195                 200

TAC TTC GCA GAT GAC GAC AAC ACG TAC AGT CTG GAG CTC TTT GAA GAG         854
Tyr Phe Ala Asp Asp Asp Asn Thr Tyr Ser Leu Glu Leu Phe Glu Glu
205                 210                 215                 220

ATG CGC AGC ACA AGA AGG GTG TCC GTG TGG CCT GTG GCC TTT GTT GGC         902
```

```
Met Arg Ser Thr Arg Arg Val Ser Val Trp Pro Val Ala Phe Val Gly
            225                 230                 235

GGC CTT CGG TAT GAG GCC CCC CGG GTG AAT GGG GCA GGG AAA GTG GTT          950
Gly Leu Arg Tyr Glu Ala Pro Arg Val Asn Gly Ala Gly Lys Val Val
        240                 245                 250

GGC TGG AAG ACA GTC TTC GAC CCC CAC CGG CCA TTT GCA ATA GAC ATG          998
Gly Trp Lys Thr Val Phe Asp Pro His Arg Pro Phe Ala Ile Asp Met
            255                 260                 265

GCT GGA TTT GCT GTC AAC CTC CGG CTC ATC TTG CAA CGA AGC CAG GCC         1046
Ala Gly Phe Ala Val Asn Leu Arg Leu Ile Leu Gln Arg Ser Gln Ala
        270                 275                 280

TAC TTT AAG CTA CGT GGG GTA AAA GGA GGC TAC CAG GAA AGC AGT CTC         1094
Tyr Phe Lys Leu Arg Gly Val Lys Gly Gly Tyr Gln Glu Ser Ser Leu
285                 290                 295                 300

CTT CGA GAA CTT GTC ACC CTC AAT GAT CTA GAG CCC AAG GCA GCA AAC         1142
Leu Arg Glu Leu Val Thr Leu Asn Asp Leu Glu Pro Lys Ala Ala Asn
            305                 310                 315

TGT ACC AAG ATC CTG GTC TGG CAT ACG CGA ACA GAG AAG CCA GTG CTG         1190
Cys Thr Lys Ile Leu Val Trp His Thr Arg Thr Glu Lys Pro Val Leu
        320                 325                 330

GTG AAT GAG GGG AAG AAG GGC TTC ACT GAC CCC TCG GTG GAG ATC             1235
Val Asn Glu Gly Lys Lys Gly Phe Thr Asp Pro Ser Val Glu Ile
            335                 340                 345

TGAAACTACA CATGCAGGAA TCACCTTCTC AGACCCTGAT CTTGGCTTCC ATCCTCTCCC       1295

ATGACTGACA GTGACTCTGA GGCAGACTCC TGAGGAATAC CTATTATGTA TACTGAAGGC       1355

TTCCAAGAGA GCCCAGCTTG ACGCCAGGAC AAAAGACAGA GAATTTAAGC ACAGAATCCC       1415

AGACCTGTGG TTCTCTACAT CAACAAGGCC AGGGGCTTGA AGACCCAAG TTCTGGGGAT        1475

TCCCGTTGCC AGCAAAGCCT GTGCTCAGCA CACCTCCTTG GAAGCTTCCT GCATTGATGG       1535

GGCTGTGTAA GCAAGGGGAC CCTGCCTTCG AGTGATGCTG GGGTGAGGGA GGTCAGAAAA       1595

CGCCACTATT GAGTGCAGCA TGGCTGTCCA TGGCTCCCTG CTCTTGGGCC CAGCATGACT       1655

ACACAGCATG TGCCCAGCCA GGACATCCTG AAGACCAGAG AGCAGCCTGG GGCATGAAGA       1715

TGCCCCAACA CTTGTCTTTC ACACCTGCTC TTCCTCAGAG CTGCTCCCAA ATCAGAAATA      1775

CCTCTGGCTC TCCTCTGGTT CGTGTTTACA GGGCATAAGG CTGTCTTGGA TCCCACCTGG      1835

CACCCAGCCC TGCATTGGGG GAGCCTGGGC CTACCTACAG CTCCCCTTGT ACCTCAGGCT      1895

GTAGAAGAAC CAAGCCCTTC CCCGTGTCCT TCAAGCCTCC TGTGCCAGAA TCAGTCAGGT     1955

GGTGGGCCTA GAGCCAGCAC AGGTCATGGA TTGACCTGGA TTGAGAACCA AGTCACCCCA     2015

CAGTCCACAC TGCCTCTCCA ATACCCCTGG GCTGCAATGC CCCTTGCTGG GTTTGGACTG     2075

GGGAGGCAAT TGCCC                                                      2090

(2) INFORMATION FOR SEQ ID NO:2:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Asn Glu Glu Leu Trp Ala Gln Pro Ala Leu Glu Met Pro Lys
1               5                   10                  15

Arg Arg Asp Ile Leu Ala Ile Val Leu Ile Val Leu Pro Trp Thr Leu
            20                  25                  30
```

```
Leu Ile Thr Val Trp His Gln Ser Ser Leu Ala Pro Leu Leu Ala Val
         35                  40                  45

His Lys Asp Glu Gly Ser Asp Pro Arg His Glu Ala Pro Pro Gly Ala
 50                  55                  60

Asp Pro Arg Glu Tyr Cys Met Ser Asp Arg Asp Ile Val Glu Val Val
 65                  70                  75                   80

Arg Thr Glu Tyr Val Tyr Thr Arg Pro Pro Trp Ser Asp Thr Leu
             85                  90                  95

Pro Thr Ile His Val Val Thr Pro Thr Tyr Ser Arg Pro Val Gln Lys
             100                 105                 110

Ala Glu Leu Thr Arg Met Ala Asn Thr Leu Leu His Val Pro Asn Leu
             115                 120                 125

His Trp Leu Val Val Glu Asp Ala Pro Arg Arg Thr Pro Leu Thr Ala
             130                 135                 140

Arg Leu Leu Arg Asp Thr Gly Leu Asn Tyr Thr His Leu His Val Glu
145                 150                 155                 160

Thr Pro Arg Asn Tyr Lys Leu Arg Gly Asp Ala Arg Asp Pro Arg Ile
                 165                 170                 175

Pro Arg Gly Thr Met Gln Arg Asn Leu Ala Leu Arg Trp Leu Arg Glu
                 180                 185                 190

Thr Phe Pro Arg Asn Ser Thr Gln Pro Gly Val Val Tyr Phe Ala Asp
         195                 200                 205

Asp Asp Asn Thr Tyr Ser Leu Glu Leu Phe Glu Glu Met Arg Ser Thr
     210                 215                 220

Arg Arg Val Ser Val Trp Pro Val Ala Phe Val Gly Leu Arg Tyr
225                 230                 235                 240

Glu Ala Pro Arg Val Asn Gly Ala Gly Lys Val Val Gly Trp Lys Thr
                 245                 250                 255

Val Phe Asp Pro His Arg Pro Phe Ala Ile Asp Met Ala Gly Phe Ala
                 260                 265                 270

Val Asn Leu Arg Leu Ile Leu Gln Arg Ser Gln Ala Tyr Phe Lys Leu
             275                 280                 285

Arg Gly Val Lys Gly Gly Tyr Gln Glu Ser Ser Leu Leu Arg Glu Leu
290                 295                 300

Val Thr Leu Asn Asp Leu Glu Pro Lys Ala Ala Asn Cys Thr Lys Ile
305                 310                 315                 320

Leu Val Trp His Thr Arg Thr Glu Lys Pro Val Leu Val Asn Glu Gly
                 325                 330                 335

Lys Lys Gly Phe Thr Asp Pro Ser Val Glu Ile
                 340                 345
```

(2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Ala Asn Thr Leu Leu His Val Pro Asn Leu His Trp Leu Val Val
 1               5                  10                  15

Glu Asp Ala Pro Arg
             20
```

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ser Thr Gln Pro Gly Val Val Tyr Phe Ala Asp Asp Asn Thr Tyr
1               5                  10                  15
Xaa Leu Glu Leu Phe Glu Glu Met Xaa
                20                  25
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Thr Val Phe Asp Pro His Xaa Pro Phe Ala Ile Asp Met Ala Gly Phe
1               5                  10                  15
Ala Val Asn Leu Xaa Xaa
                20
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(ix) FEATURE:
        (A) NAME/KEY: misc_feature
        (B) LOCATION: 1..18
        (D) OTHER INFORMATION: /note= "N AT POSITION 3 IS INOSINE"

(xi) SEQUENCE DESCRIPTION: SEQ ID NO:6:

```
GTNCCNAAYY TNCAYTGG                                              18
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:7:

```
TANGTRTTRT CRTCRTC                                               17
```

(2) INFORMATION FOR SEQ ID NO:8:

(i) SEQUENCE CHARACTERISTICS:

-continued

```
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:8:

TCRTCRTCNG CRAARTA                                                  17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:9:

TAYTTYGCNG AYGAYGA                                                  17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:10:

TTTGCNGAYG AYGAYAA                                                  17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:11:

ACNGCRAANC CNGCCAT                                                  17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:12:

CTGGTGGTGG AGGATGC                                                  17

(2) INFORMATION FOR SEQ ID NO:13:
```

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:13:

GTCTATTGCA AATGGCC                                                     17

(2) INFORMATION FOR SEQ ID NO:14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:14:

TGAAGGTTGG GCACAT                                                      16

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:15:

TAGVGTGTTG GCCATT                                                      16

(2) INFORMATION FOR SEQ ID NO:16:

(i) SEQUENCE CHARACTERISTICS:
        (A) LENGTH: 411 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

CTGGTGGTGG AGGATGCTCC ACGTAGGACG CCCCTCACAG CGCGCCTGCT GCGCGACACT       60

GGCCTCAACT ATACACACCT GCACGTAGAG ACACCACGCA ACTACAAGCT GCGAGGTGAC      120

GCCCGAGACC CTCGCATCCC ACGTGGCACC ATGCAGCGCA ATCTGGCCCT GCGCTGGTTG      180

CGGGAGACCT TCCCACGGAA CTCCACTCAG CCGGGTGTAG TGTACTTCGC AGATGACGAC      240

AACACGTACA GTCTGGAGCT CTTTGAAGAG ATGCGCAGCA CAAGAAGGGT GTCCGTGTGG      300

CCTGTGGCCT TTGTTGGCGG CCTTCGGTAT GAGGCCCCCC GGGTGAATGG GGCAGGGAAA      360

GTGGTTGGCT GGAAGACAGT CTTCGACCCC CACCGGCCAT TTGCAATAGA C              411

(2) INFORMATION FOR SEQ ID NO:17:

(i) SEQUENCE CHARACTERISTICS:
        (A) LENGTH: 1674 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO:17:

GACATCGTGG AGGTGGTGCG CACAGAGTAC GTGTACACGA GGCCGCCACC GTGGTCCGAC      60

ACGCTGCCCA CCATCCATGT GGTGACGCCC ACCTACAGTA GACCGGTGCA GAAGGCAGAG     120

CTGACGCGAA TGGCCAACAC GCTATTGCAT GTGCCCAACC TTCACTGGCT GGTGGTGGAG     180

GATGCTCCAC GTAGGACGCC CCTCACAGCG CGCCTGCTGC GCGACACTGG CCTCAACTAT     240

ACACACCTGC ACGTAGAGAC ACCACGCAAC TACAAGCTGC GAGGTGACGC CCGAGACCCT     300

CGCATCCCAC GTGGCACCAT GCAGCGCAAT CTGGCCCTGC GCTGGTTGCG GGAGACCTTC     360

CCACGGAACT CCACTCAGCC GGGTGTAGTG TACTTCGCAG ATGACGACAA CACGTACAGT     420

CTGGAGCTCT TTGAAGAGAT GCGCAGCACA AGAAGGGTGT CCGTGTGGCC TGTGGCCTTT     480

GTTGGCGGCC TTCGGTATGA GGCCCCCCGG GTGAATGGGG CAGGGAAAGT GGTTGGCTGG     540

AAGACAGTCT TCGACCCCCA CCGGCCATTT GCAATAGACA TGGCTGGATT TGCTGTCAAC     600

CTCCGGCTCA TCTTGCAACG AAGCCAGGCC TACTTTAAGC TACGTGGGGT AAAAGGAGGC     660

TACCAGGAAA GCAGTCTCCT TCGAGAACTT GTCACCCTCA ATGATCTAGA GCCCAAGGCA     720

GCAAACTGTA CCAAGATCCT GGTCTGGCAT ACGCGAACAG AGAAGCCAGT GCTGGTGAAT     780

GAGGGGAAGA AGGGCTTCAC TGACCCCTCG GTGGAGATCT GAAACTACAC ATGCAGGAAT     840

CACCTTCTCA GACCCTGATC TTGGCTTCCA TCCTCTCCCA TGACTGACAG TGACTCTGAG     900

GCAGACTCCT GAGGAATACC TATTATGTAT ACTGAAGGCT TCGAAGAGAG CCCAGCTTGA     960

CGCCAGGACA AAAGACAGAG AATTTAAGCA CAGAATCCCA GACCTGTGGT TCTCTACATC    1020

AACAAGGCCA GGGGCTTGAA AGACCCAAGT TCTGGGGATT CCCGTTGCCA GCAAAGCCTG    1080

TGCTCAGCAC ACCTCCTTGG AAGCTTCCTG CATTGATGGG GCTGTGTAAG CAAGGGGACC    1140

CTGCCTTCGA GTGATGCTGG GGTGAGGGAG GTCAGAAAAC GCCACTATTG AGTGCAGCAT    1200

GGCTGTCCAT GGCTCCCTGC TCTTGGGCCC AGCATGACTA CACAGCATGT GCCCAGCCAG    1260

GACATCCTGA AGACCAGAGA GCAGCCTGGG GCATGAAGAT GCCCCAACAC TTGTCTTTCA    1320

CACCTGCTCT TCCTCAGAGC TGCTCCCAAA TCAGAAATAC CTCTGGCTCT CCTCTGGTTC    1380

GTGTTTACAG GCATAAGGC TGTCTTGGAT CCCACCTGGC ACCCAGCCCT GCATTGGGGG    1440

AGCCTGGGCC TACCTACAGC TCCCCTTGTA CCTCAGGCTG TAGAAGAACC AAGCCCTTCC    1500

CCGTGTCCTT CAAGCCTCCT GTGCCAGAAT CAGTCAGGTG GTGGGCCTAG AGCCAGCACA    1560

GGTCATGGAT TGACCTGGAT TGAGAACCAA GTCACCCCAC AGTCCACACT GCCTCTCCAA    1620

TACCCCTGGG CTGCAATGCC CCTTGCTGGG TTTGGACTGG GGAGGCAATT GCCC          1674

(2) INFORMATION FOR SEQ ID NO:18:

(i) SEQUENCE CHARACTERISTICS:
        (A) LENGTH: 560 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

GCGCGCGCAT CGCAGGGCAG CAGCCCTGGG TCTCTGGGGC CAGGGCATAG GACTGCCACC      60

CGCTATGGAC CGCGCCAGGG ACGATATGGA CTCGCTGCCG CAGGTATCAA CCTCCGAAGG     120

```
TTCCTGACCC TGCGCTGGAC TACTTCCCCT TCGCAGACTC CCATCAGGCC GGACTCTGCA      180

AACCTGCTGC CACAATGGGT AATGAGGAGC TGTGGGCGCA GCCAGCCTTG GAGATGCCGA      240

AGAGAAGGGA CATCCTCGCG ATTGTCCTCA TTGTGCTTCC CTGGACACTG CTCATCACCG      300

TCTGGCACCA GAGCAGCCTC GCACCTCTGC TTGCTGTGCA CAAGGATGAG GGAAGTGACC      360

CCCGCCATGA GGCACCACCC GGTGCGGACC CTAGGGAGTA CTGCATGTCC GACCGTGACA      420

TCGTGGAGGT GGTGCGCACA GAGTACGTGT ACACGAGGCC GCCACCGTGG TCCGACACGC      480

TGCCCACCAT CCATGTGGTG ACGCCCACCT ACAGTAGACC GGTGCAGAAG GCAGAGCTGA      540

CGCGAATGGC CAACACGCTA                                                 560

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:19:

TCCGAATTCT GACATCGTGG AGGTGGTGCG CACA                                  34

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:20:

ATTGGATCCT GTGTAGTTTC AGATCTCCAC CGA                                   33
```